(12) United States Patent
Liu et al.

(10) Patent No.: US 8,213,573 B2
(45) Date of Patent: Jul. 3, 2012

(54) SYSTEM AND METHOD FOR MONITORING X-RAYS RECEIVED BY A PORTABLE IMAGING DETECTOR

(75) Inventors: James Zhengshe Liu, Glenview, IL (US); Feng (Frank) Gao, Naperville, IL (US); Chuande Liu, Waukesha, WI (US); Ping Xue, Pewaukee, WI (US); Jon Omernick, Wauwatosa, WI (US); Donald Langler, Brookfield, WI (US)

(73) Assignee: General Electric Company, Schenectady, NY (US)

( * ) Notice: Subject to any disclaimer, the term of this patent is extended or adjusted under 35 U.S.C. 154(b) by 240 days.

(21) Appl. No.: 12/763,841

(22) Filed: Apr. 20, 2010

(65) Prior Publication Data

US 2011/0255666 A1    Oct. 20, 2011

(51) Int. Cl.
*G01N 23/04* (2006.01)
(52) U.S. Cl. ......................................... 378/62; 378/96.8
(58) Field of Classification Search .................... 378/62, 378/98.8
See application file for complete search history.

(56) References Cited

U.S. PATENT DOCUMENTS

| | | | |
|---|---|---|---|
| 6,516,098 B2 * | 2/2003 | Nonaka | 382/274 |
| 6,977,988 B2 | 12/2005 | Niwa | 378/95 |
| 6,999,121 B2 | 2/2006 | Endo | 348/297 |
| 7,541,591 B2 | 6/2009 | Endo et al. | 250/369 |
| 7,601,962 B2 | 10/2009 | Petrick et al. | 250/370.09 |

* cited by examiner

*Primary Examiner* — Courtney Thomas
(74) *Attorney, Agent, or Firm* — The Small Patent Law Group; Dean D. Small

(57) ABSTRACT

A method for imaging an object includes radiating the object of interest and sensing the radiation that penetrates through the object using a detector having at least one active area and at least one inactive area, determining when the radiation is completed using information received from the inactive area of the imaging detector, and reconstructing an image of the object using information received from the active area of the imaging detector. A medical imaging system and a computer-readable medium are also provided.

20 Claims, 12 Drawing Sheets

SYSTEM AND METHOD FOR MONITORING X-RAYS RECEIVED BY A PORTABLE IMAGING DETECTOR

BACKGROUND OF THE INVENTION

The subject matter disclosed herein relates generally to imaging detectors, and more particularly to a method and system for monitoring X-rays received by a portable imaging detector.

Different imaging modalities use different types of detectors to detect emitted, transmitted or reflected energy from an imaging source. X-rays are one type of energy detected by a detector. There are different types of X-ray imaging systems that use different types of X-ray detectors. For example, in an analog computed radiography (CR) system, the X-ray source is activated by the operator using, for example, a switch and. deactivated by a timer. The X-rays attenuated by the patient are recorded on the X-ray film or CR cassette.

In a digital radiographic system, the use of portable digital detectors has been increasing considerably due to the convenience, superior workflow and high image quality produced by the portable digital detectors. However, portable digital detectors currently need to be coupled to a digital imaging system in order to function. Therefore, the analog imaging system is modified to include a digital controller that controls the operation of the X-ray source. Moreover, the X-ray film or cassette is replaced with a digital X-ray detector that works independently from the X-ray source. Specifically, the digital X-ray detector functions independently from the X-ray source in an operational mode referred to herein as a non-integrated mode. In the non-integrated mode of operation, the X-ray source is activated by the operator using, for example, the switch and deactivated by a timer. X-rays attenuated by the patient are then recorded on the digital X-ray detector. The digital X-ray detector is then read or alternatively scrubbed on a row-by-row basis using the digital imaging system.

Reading is performed whenever an image, acquired by the digital X-ray detector, includes exposure data or alternatively offset data. Scrubbing is similar to reading except that data acquired from scrubbing is not clinically relevant, and is therefore not used to reconstruct an image of the object. Scrubbing is performed to maintain proper bias on the digital X-ray detector photodiodes during idle periods. Specifically, scrubbing is performed to keep the detector ready for use largely due to the less than ideal characteristics of amorphous silicon used to fabricate the detector.

However, because the digital X-ray detector is not integrated with the X-ray source, an operator may inadvertently command the digital imaging system to read data from the X-ray detector prior to the conclusion of the X-ray examination. As a result, useful diagnostic information may be discarded resulting in only a partial image or a degraded image.

BRIEF DESCRIPTION OF THE INVENTION

In one embodiment, method for imaging an object is provided. The method includes radiating an object of interest and measuring the radiation that penetrates through the object using a detector having at least one active area and at least one inactive area, determining when the radiation is completed using information received from the inactive area of the imaging detector, and reconstructing an image of the object using information received from the active area of the imaging detector.

In another embodiment, a medical imaging system is provided. The medical imaging system includes a portable X-ray detector configured to receive X-rays from an X-ray source, and a detector controller coupled to the portable X-ray detector. The detector controller is configured to determine when an X-ray exposure of an object has been initiated, select an active area and an inactive area on an imaging detector, determine when the exposure is completed using information received from the inactive area of the imaging detector, and reconstruct an image of the object using information received from the active area of the imaging detector.

In a further embodiment, a non-transitory computer-readable medium encoded with a program is provided. The computer-readable medium is configured to determine when an X-ray exposure of an object has been initiated, select an active area and an inactive area on an imaging detector, determine when the exposure is completed using information received from the inactive area of the imaging detector, and reconstruct an image of the object using information received from the active area of the imaging detector.

DETAILED DESCRIPTION OF THE INVENTION

Figure 1:
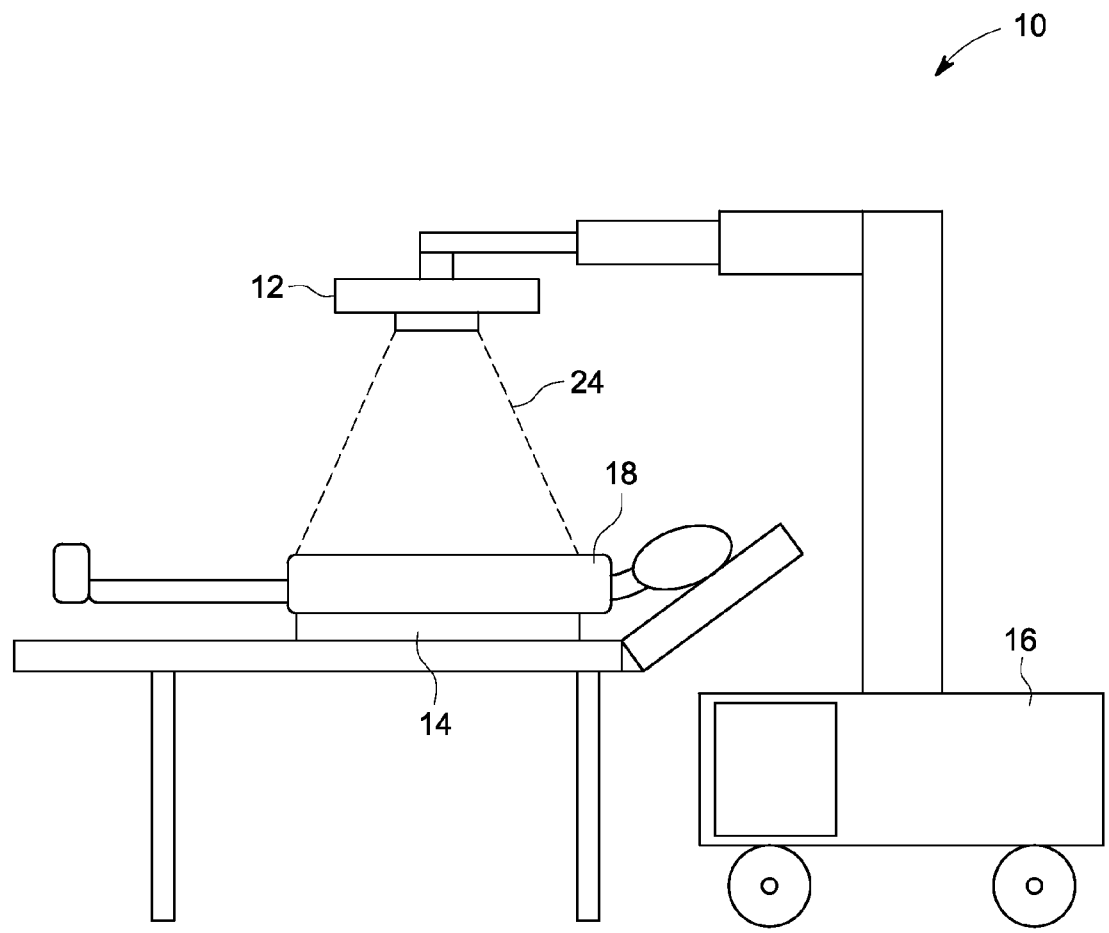
FIG. 1 is a pictorial view of an exemplary medical imaging system in accordance with an embodiment of the present invention.

The foregoing summary, as well as the following detailed description of certain embodiments of the present invention, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand alone programs, may be incorporated as subroutines in an operating system, may be functions in an installed software package, and the like. It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Also as used herein, the phrase "reconstructing an image" is not intended to exclude embodiments of the present invention in which data representing an image is generated but a viewable image is not. Therefore, as used herein the term "image" broadly refers to both viewable images and data representing a viewable image. However, many embodiments generate, or are configured to generate, at least one viewable image.

Figure 2:
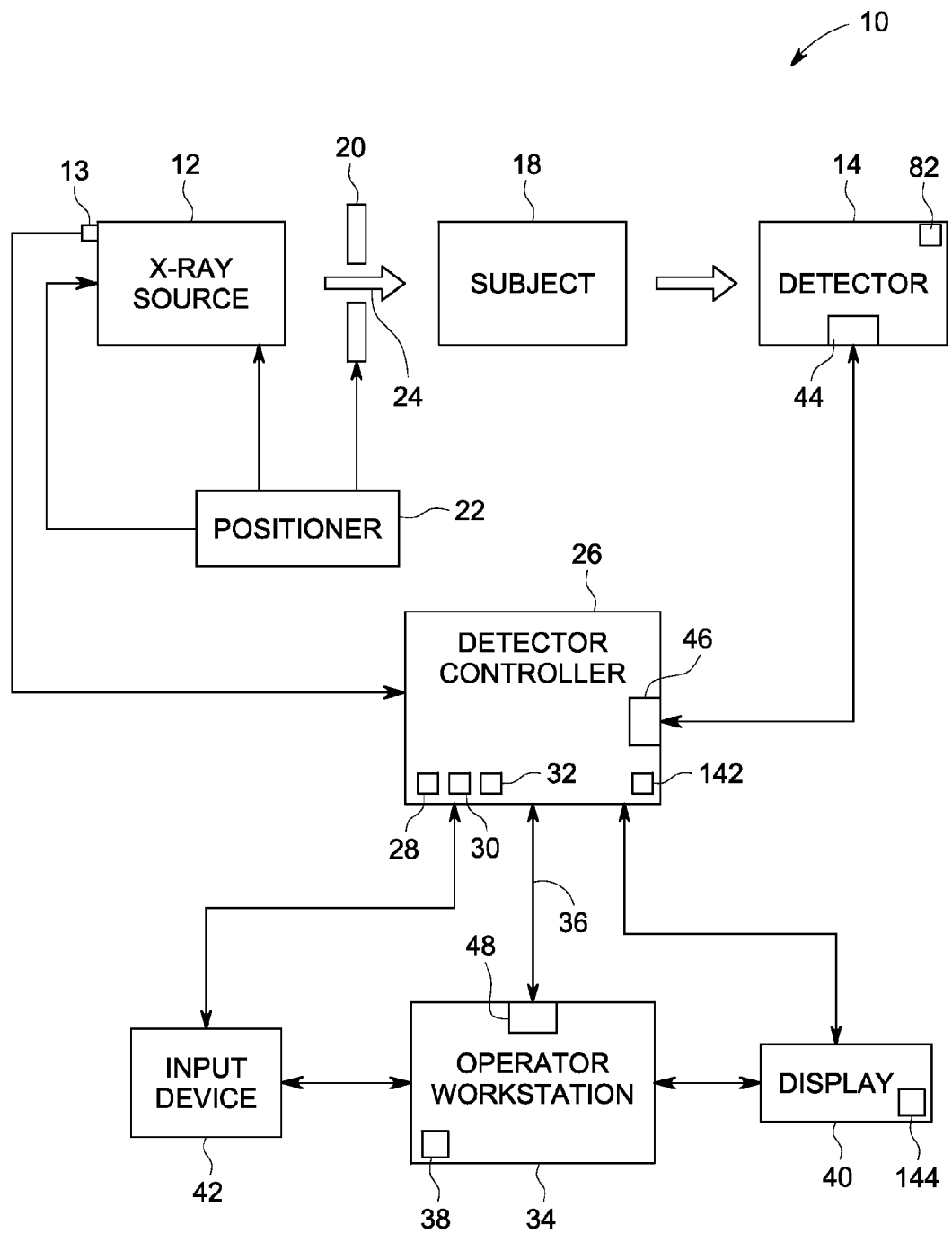
FIG. 2 is a block schematic diagram of the exemplary medical imaging system shown in FIG. 1 in accordance with an embodiment of the present invention.

Referring to the drawings, FIG. 1 is a pictorial view of an exemplary imaging system 10 provided in accordance with an embodiment of the present invention. FIG. 2 is a block schematic diagram of the exemplary imaging system 10 shown in FIG. 1. Various embodiments of the invention may be used with the exemplary medical imaging system 10 as shown in FIGS. 1 and 2. The medical imaging system 10 may be any type imaging system. In the exemplary embodiment, imaging system 10 is an x-ray imaging system. Moreover, the various embodiments are not limited to medical imaging systems for imaging human subjects, but may include veterinary or non-medical systems for imaging non-human objects, or non-destructive testing systems (e.g. airport baggage systems) etc.

The medical imaging system 10 in some embodiments is a digital radiography imaging system 10 that includes an X-ray source 12 and a detector 14. In one exemplary embodiment, the detector 14 is not integrated with the X-ray source 12 shown in FIG. 1. The x-ray source 12 is mounted to a gantry 16. The gantry 16 is movable to enable the x-ray source 12 to be properly positioned with respect to a subject 18 being imaged or to enable the x-ray source 12 to be moved from one imaging room to another. Optionally, the gantry 16 is stationarily mounted by coupling the gantry to a floor, for example. Referring to FIG. 2, the imaging system 10 may also include a collimator 20 that is disposed between the x-ray source 12 and the subject 18. The imaging system 10 may also include a positioner 22. The positioner 22 is a mechanical controller coupled to the x-ray source 12 and collimator 20 for controlling the positioning of the x-ray source 12 and the collimator 20.

The X-ray source 12 is activated and/or deactivated using a switch 13. During operation, the imaging system 10 generates images of the subject 18 using an x-ray beam 24 emitted by the x-ray source 12, and passing through the collimator 20. The collimator 20 forms and confines the x-ray beam 24 to a desired region, wherein the subject 18, such as a human patient, an animal or an object, is positioned. A portion of the x-ray beam 24 passes through or around the subject 18 and, being altered by attenuation and/or absorption by tissues within the subject 18, continues on toward and impacts the detector 14. In one embodiment, the detector 14 may be a fixed detector that is mounted in a fixed position. In the exemplary embodiment, the detector 14 is a portable digital flat panel X-ray detector that is not integrated with the X-ray source 12. Specifically, the detector 14 is not controlled by the X-ray source 12. Rather, the detector 14 is controlled by a detector controller, discussed below. During operation, the detector 14 converts x-ray photons received on its surface to lower energy light photons, and subsequently to electric signals, which are acquired and processed to reconstruct an image of internal anatomy of the subject 18.

The imaging system 10 further includes a detector controller 26 that is coupled to the detector 14 for controlling operation of the detector 14. In the exemplary embodiment, the detector controller 26 also receives an input from the switch 13. The detector controller 26 may supply both power and control signals for imaging examination sequences. In general, the detector controller 26 controls the operation of the detector 14 to process acquired image data. The detector controller 26 may also include signal processing circuitry, based on a general purpose or application-specific computer, associated memory circuitry for storing programs and routines executed by the computer, as well as configuration parameters and image data, interface circuits, and so forth. Specifically, the detector controller 26 may include at least one computer or processor 28 that is configured to coordinate the operation of the detector 14 to process image data acquired from the detector 14. As used herein, the term "computer" may include any processor or processor-based system including systems using controllers, reduced instruction set circuits (RISC), application specific integrated circuits (ASICs), logic circuits, and any other circuit or processor capable of executing the functions described herein. The above examples are exemplary only, and are thus not intended to limit in any way the definition and/or meaning of the term "computer". During operation, the processor 28 carries out various functionality in accordance with routines stored in an associated memory device 30. The associated memory device 30 may also serve to store configuration parameters, imaging protocols, operational logs, raw and/or processed image data, and so forth.

The detector controller 26 may further includes a device 32 that permits an operator or user to define imaging protocols, imaging sequences, determine the operational status and health of system components. The device 32 may allow external devices to receive images and image data, and command operation of the radiography system, configure parameters of the imaging system 10.

The detector controller 26 may be coupled to a range of external devices via a communications interface. Such devices may include, for example, an operator workstation 34 for interacting with the detector controller 26 or directly to the imaging system, processing or reprocessing images, viewing images, and so forth. The operator workstation 34 may be embodied as a personal computer (PC) that is positioned near the imaging system 10 and hard-wired to the detector controller 26 via a communication link 36. The workstation 34 may also be embodied as a portable computer such as a laptop computer or a hand-held computer that transmits information to the detector controller 26. In one embodiment, the communication link 36 may be hardwired between the detector controller 26 and the workstation 34. Optionally, the communication link 36 may be a wireless communication link that enables information to be transmitted to or from the workstation to the detector controller 26 wirelessly. In the exemplary embodiment, the workstation 34 controls real-time operation of the imaging system 10. The workstation 34 is also programmed to perform medical image diagnostic acquisition and reconstruction processes described herein.

Accordingly, the operator workstation 34 includes a central processing unit (CPU) or computer 38, a display 40 and an input device 42. In the exemplary embodiment, the computer 38 executes a set of instructions that are stored in one or more storage elements or memories, in order to process input data. The storage elements may also store data or other information as desired or needed. The storage element may be in the form of an information source or a physical memory element within the computer 38. The set of instructions may include various commands that instruct the computer or processor 38 as a processing machine to perform specific operations such as the methods and processes of the various embodiments described herein. The set of instructions may be in the form of a software program. As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

The software may be in various forms such as system software or application software. Further, the software may be in the form of a collection of separate programs, a program module within a larger program or a portion of a program module. The software also may include modular programming in the form of object-oriented programming. The processing of input data by the processing machine may be in response to user commands, or in response to results of previous processing, or in response to a request made by another processing machine.

The CPU 38 connects to the communication link 36 and receives inputs, e.g., user commands, from the input device 42. The input device 42 may be, for example, a keyboard, mouse, a touch-screen panel, and a voice recognition system, etc. Through input device 42 and associated control panel switches, the operator can control the operation of the imaging system 10 and the positioning of the x-ray source 12 for a scan. Similarly, the operator can control the display of the resulting image on the display 40 and can perform image-enhancement functions using programs executed by the workstation CPU 38. The workstation 34 may also be linked to the detector controller 26 by any one or more network links.

In the exemplary embodiment, to transmit the electric signals from the detector 14 to the detector controller 26 or the workstation 34, the detector 14 includes a transceiver 44 that is configured to transmit the electrical signals and other information generated by the detector 14 in a wireless format to a corresponding transceiver 46 that is mounted in the detector controller 26. Optionally, the transceiver 44 is configured to transmit the electrical signals and other information generated by the detector 14 in a wireless format to a corresponding transceiver 48 that is mounted in the workstation 34.

Figure 3:
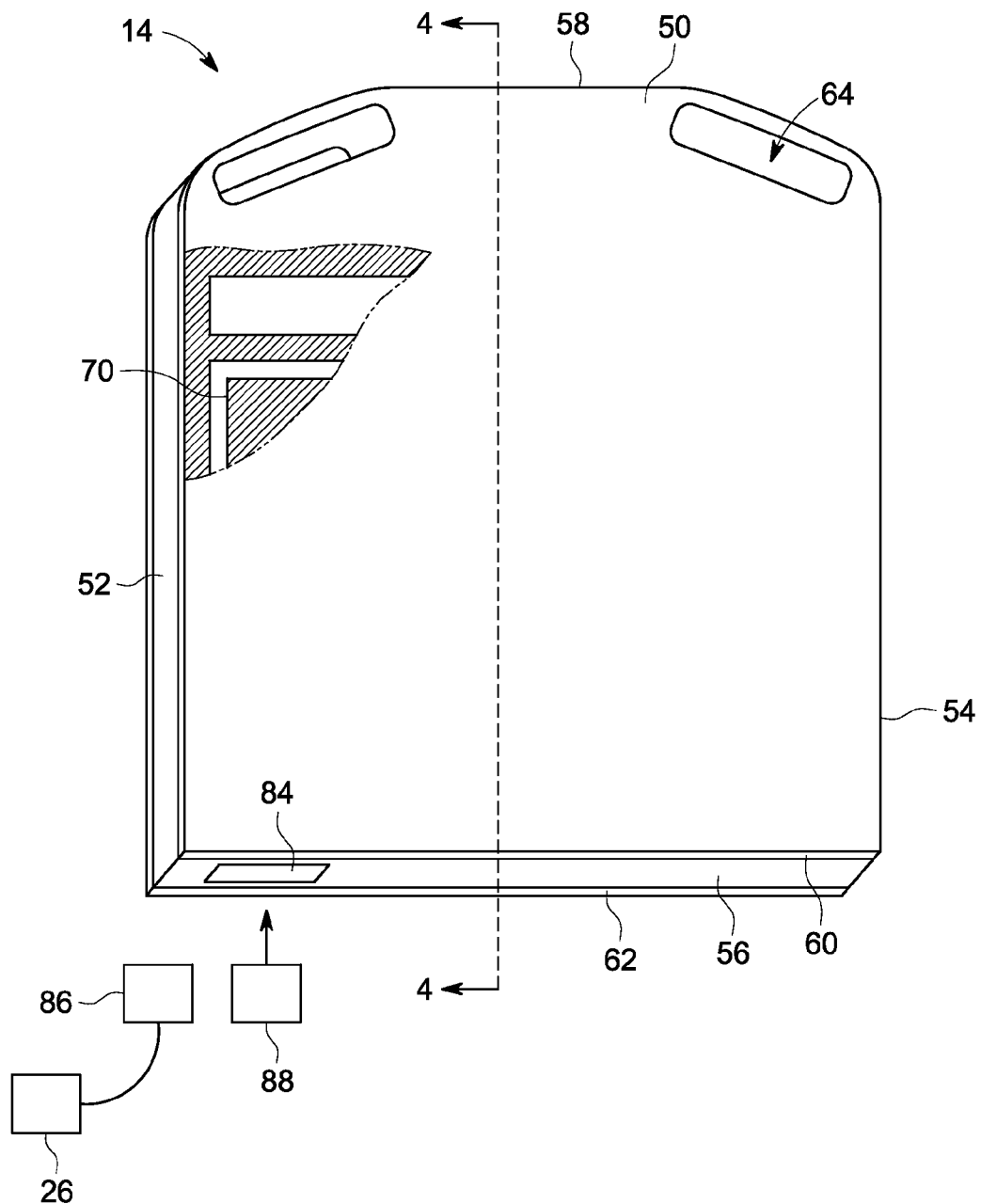
FIG. 3 is a top cut-away view of the exemplary X-ray detector shown in FIGS. 1 and 2 in accordance with an embodiment of the present invention.

FIG. 3 is a bottom cut-away view of the exemplary portable detector 14 shown in FIGS. 1 and 2. In the exemplary embodiment, the portable detector 14 is hand-carried by an operator to various locations to perform medical imaging. Additionally, the portable detector 14 may be mounted on a wheeled cart or other movable apparatus to enable an operator to move the detector 14 from one location to another location.

As shown in FIG. 3, the portable detector 14 includes a casing 50. The casing 50 is formed to include a pair of sidewalls 52 and 54, a bottom side 56, and an opposing top side 58. The casing 50 also includes a front cover 60, shown as a surface parallel to the plane of the illustration, and an opposing back cover 62. The casing also includes a handle 64 that extends from the front cover 60 to the back cover 62. During operation, the handle 64 enables an operator to transport the portable detector 14. Specifically, the handle 64 can be used to mount, carry and/or store the portable detector 14. The sidewalls, top and bottom walls, the front and back covers together form the casing 50. The casing 50 may be made of a lightweight, low atomic number (N) material, such as aluminum, or a graphite material. Graphite has a lower weight than aluminum, but it is also stiffer and less energy-absorbent.

Figure 4:
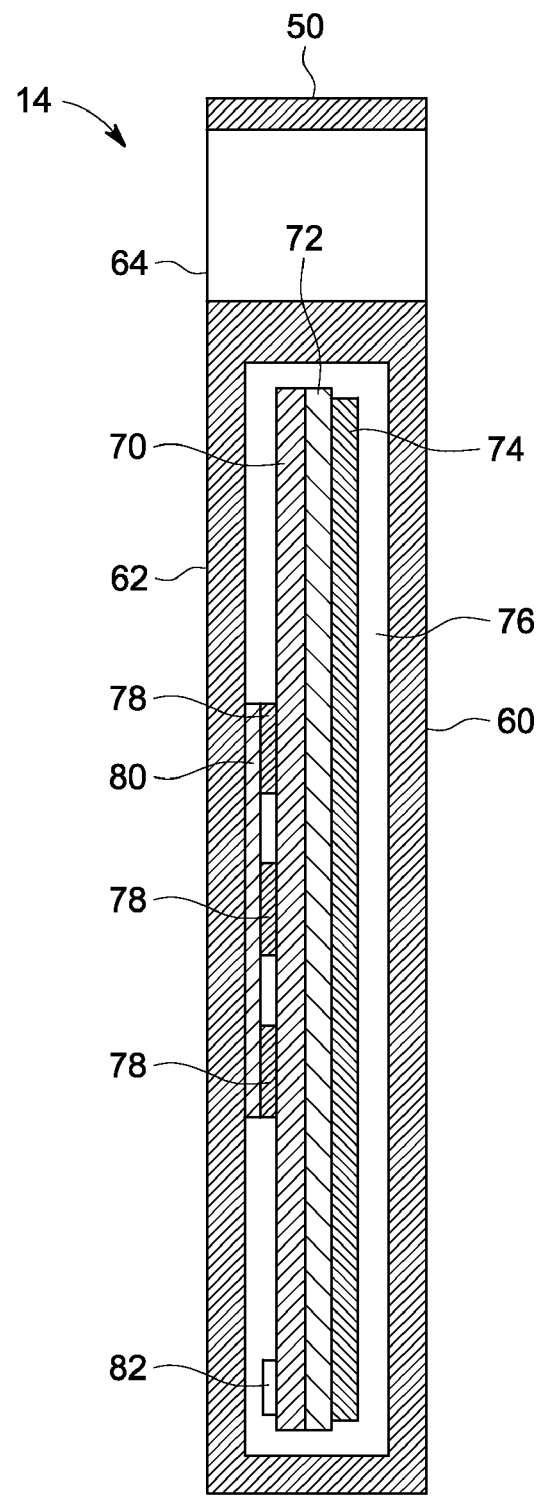
FIG. 4 is a side cut-away view of the detector shown in FIG. 3.

FIG. 4 is a side cut-away view of the portable detector 14 shown in FIG. 3 viewed along the line 4-4 of FIG. 3. As shown in FIG. 4, the detector 14 also includes a circuit board 70 that is affixed to a panel support 72 that may be fabricated from a low N material, which in turn is affixed (e.g., using an adhesive) to a photo-detector array 74. The photo-detector array 74 is discussed in more detail below. To provide some degree of break resistance for the photo-detector array 74, a gap 76 is provided between the photo-detector array 74 and the front cover 60. Also, the electronic assembly is clear of any wall of the casing, but is mounted to the back cover 62. Additionally, heat generating components 78 on the circuit board 70 may be thermally coupled to back cover 62 using a heat conducting compound 80. The heat conducting compound 80 provides, directly or indirectly, a mechanical coupling between the circuit board 70 and the back cover 62. In the exemplary embodiment, the portable detector 14 also includes a processor 82. In the exemplary embodiment, the processor 82 is mounted to the circuit board 70. The processor 82 is configured to store information to operate the portable detector 14 and/or to transmit information to a remote location via the wireless transceiver 44 as discussed above.

In the exemplary embodiment, the detector 14 is portable, but typically large enough to image a significant region of a human patient, such as a patient's chest. Thus, the portable detector 14 may be only about one or a few centimeters in thickness, but may be tens of centimeters in width and length. In one embodiment, the portable detector 14 also includes an x-ray grid or anti-scatter grid, or some other grid appropriate for medical x-ray imaging. Referring again to FIG. 3, the portable detector also includes a receptacle 84 that is configured to receive either a tether 86 or a battery 88. The tether 86 is embodied as a hardwired cable that enables a remote station such as, the controller 26 to provide power to and communicate with the portable detector 14. Optionally, the portable detector 14 may be operated using the battery 88 and communicate with a remote station via the wireless links discussed above.

Figure 5:
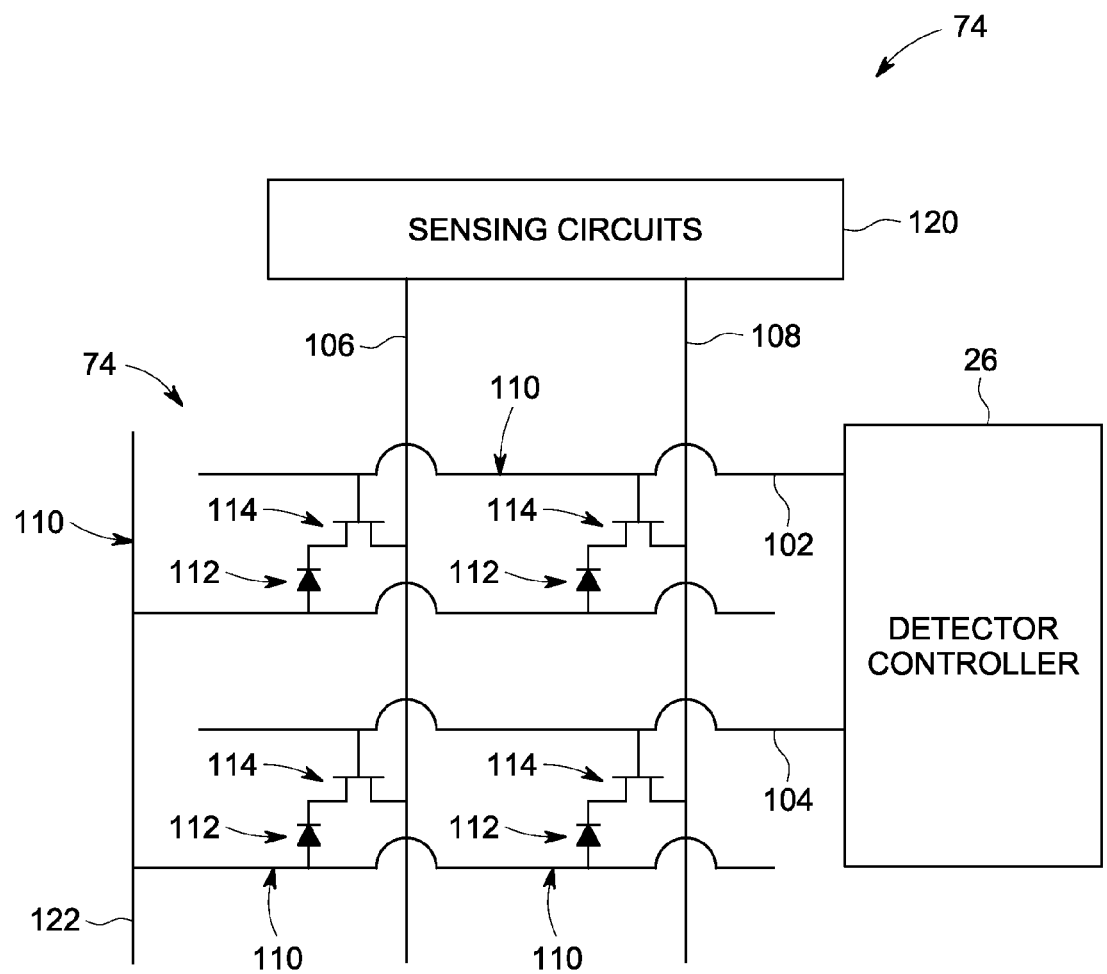
FIG. 5 is a schematic diagram of the exemplary X-ray detector shown in FIGS. 1 and 2 in accordance with an embodiment of the present invention.

FIG. 5 is a circuit diagram of an embodiment of the photo-detector array 74 shown in FIG. 4. The photo-detector array 74 includes a plurality of scan lines 102 and 104, and a plurality of data lines 106 and 108. The photo-detector array 74 is formed by a matrix of pixels or detector elements 110. The detector elements 110 are arranged on a substrate (not shown). Each detector element 110 includes a photodiode 112 made of a material, such as silicon. Examples of silicon include amorphous silicon and crystalline silicon. Moreover, each detector element 110 includes a field effect transistor (FET) 114. The photodiode 112 is fabricated over a large portion of the detector element 110 in order that the photodiode 112 will intercept a sizeable portion of the light produced by a scintillator layer (not shown). Each photodiode 112 has a capacitance that allows the photodiode 112 to store an electrical charge, which is then partially or alternatively wholly discharged due to an excitation by the lower energy photons of the portion of one of X-ray beams emitted from the X-ray source 12.

The cathode of each photodiode 112 in each detector element 110 of each column of the photo detector array 74 is connected via a source-drain conduction path of the FET 114 to one of data lines 106 and 108. The data lines 106 and 108 are connected to a plurality of sensing circuits 120. The sensing circuits 120 maintain the data lines 106 and 108 at a relatively constant potential at all times. In the exemplary embodiment, the sensing circuits 120 are included in the X-ray detector 14. The anode of each photodiode 112 is connected to a common electrode 122. A gate electrode of FET 114 in each row is connected to one of the scan lines 102 and 104. Each scan line 102 and 104 runs the full dimension of the detector 14. The scan lines 102 and 104 are in communication with the detector controller 26. In the exemplary embodiment, the photo-detector array 74 includes m scan lines 102/104 and any integer, n, data lines 106/108.

Figure 6:
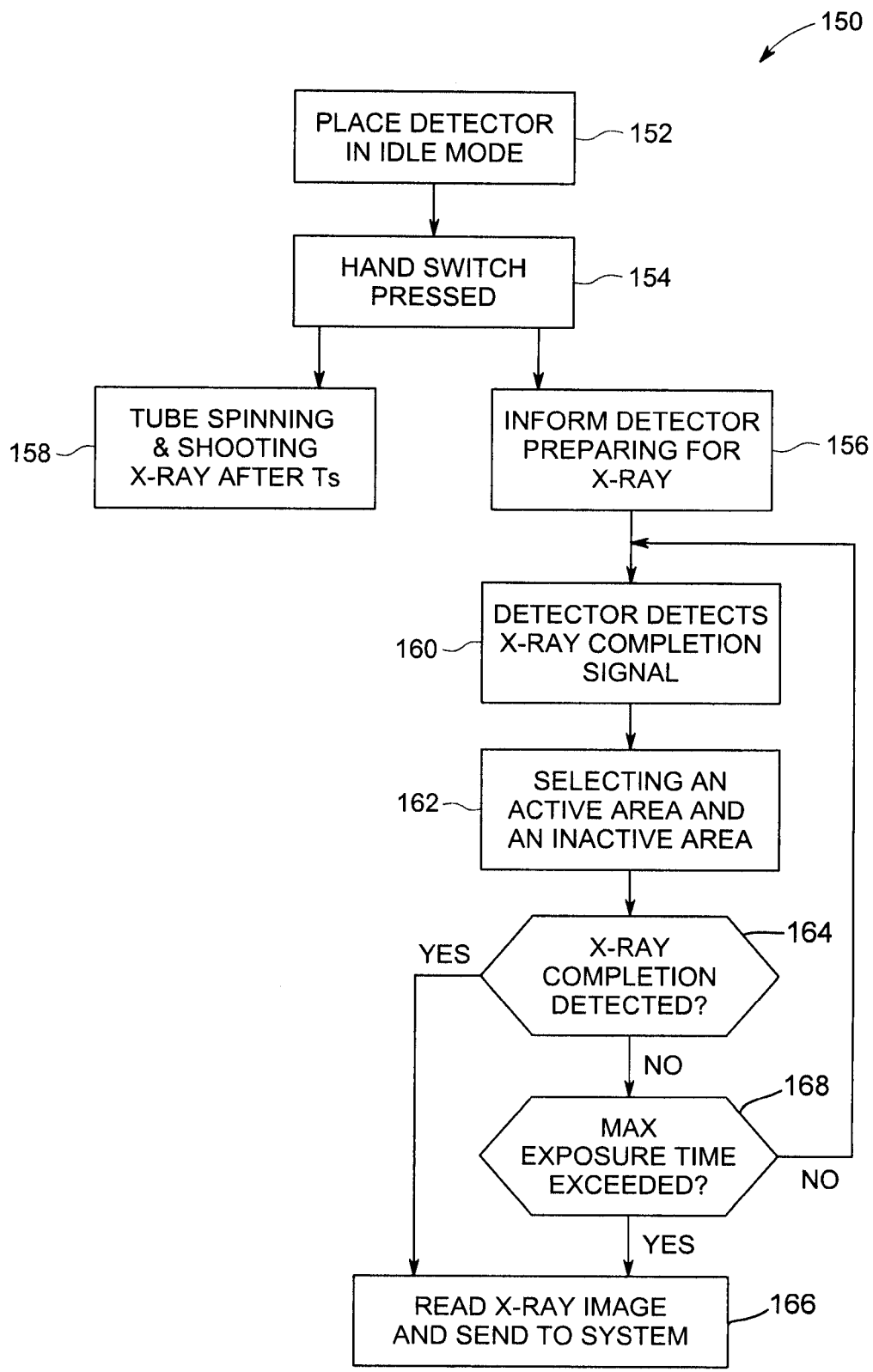
FIG. 6 is a flowchart of an exemplary method of operating the medical imaging system shown in FIGS. 1 and 2 in accordance with an embodiment of the present invention.
Figure 7:
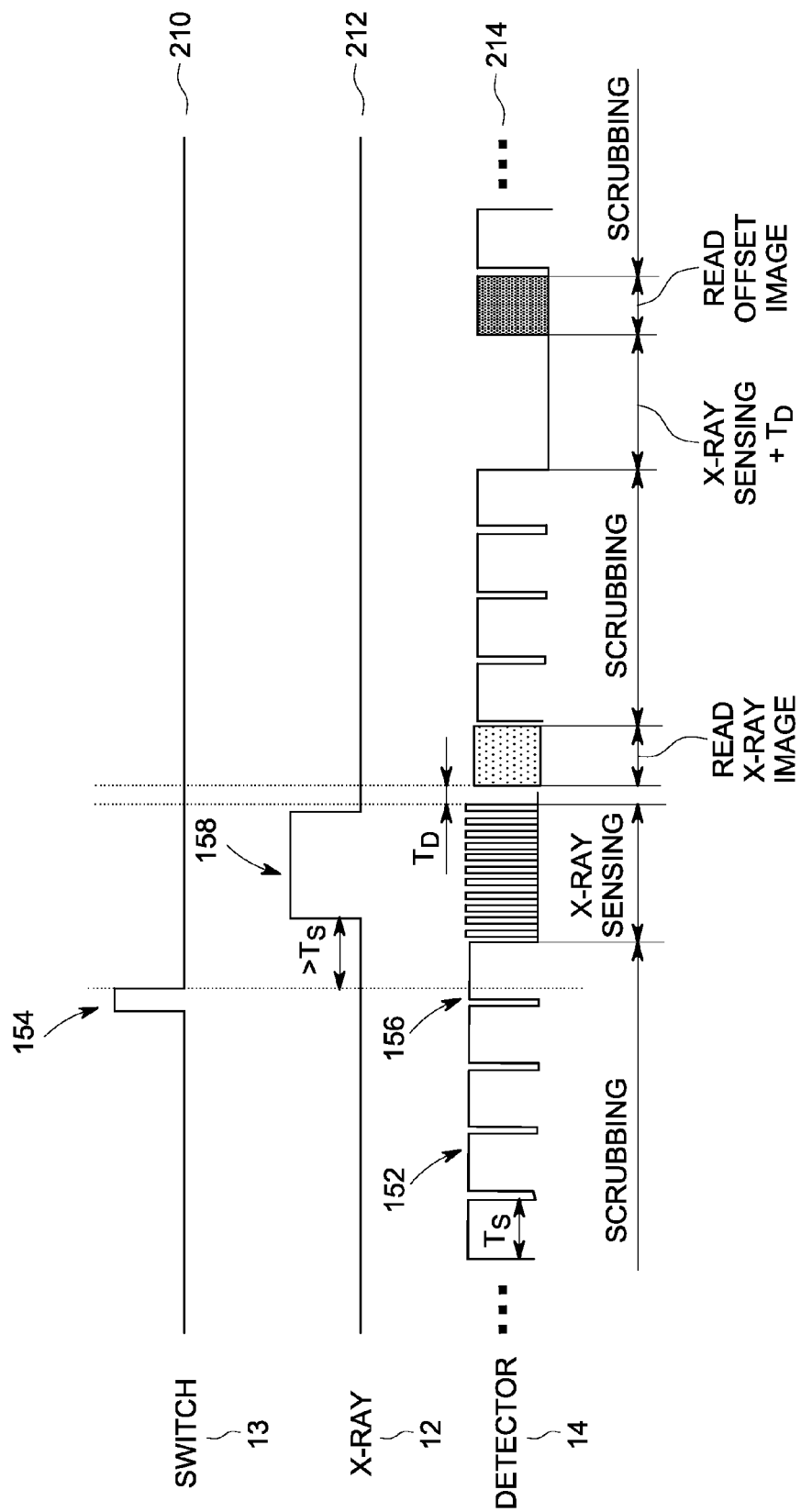
FIG. 7 is an exemplary timing diagram in accordance with an embodiment of the present invention.

FIG. 6 is a flowchart illustrating an exemplary method 150 of reading data from the detector 14. FIG. 7 is an exemplary timing diagram 200 illustrating one implementation of the method shown in FIG. 6. At 152, the detector 14 is initially configured to operate in an idle mode. In the idle mode of operation, the entire detector 14 is continually scrubbed to remove diode leakage and to maintain a known potential or a known voltage on the photodiodes 112 during idle periods. For example, assuming that the detector 14 includes 2048 columns and 2048 rows of detector elements 110, each of the rows and columns is scrubbed to maintain proper bias on the digital X-ray detector photodiodes during idle periods. Scrubbing also facilitates reducing a plurality of effects of image retention or lag, and/or protects a plurality of operating characteristics of the FETs 114. In the exemplary embodiment, the sensing circuits 120 restore the charge of the photodiodes 112 during scrubbing. The time required to perform a single scrub of the detector 14 is denoted as $T_S$. In the exemplary embodiment, $T_S$ is between approximately 0.125 milliseconds and 0.250 milliseconds.

During the detector scrub performed at 152, the photodiodes 112 continue to store charge until a voltage across the photodiodes 112 is equal to a voltage difference between a corresponding one of data lines 106/108 and the common electrode 122 and until the photodiodes 112 are each charged to the known voltage, after which the FETs 114 are switched off. For example, the photodiodes 112 continue to store charge until a voltage across the photodiodes 112 is equal to a voltage difference between the data lines 106/108 and the common electrode 122. At the completion of scrubbing, the FETs 114 are switched off by the detector controller 26.

At 154, the detector controller 26 receives a signal from the switch 13 that the X-ray source 12 has been activated. At 156, the detector controller 26 transmits the signal to the detector 14. At 158, the system controller (not shown) instructs the X-ray source 12 to begin transmitting X-rays to the detector 14 after the predetermined time-period $T_S$. In the exemplary embodiment, the signal is transmitted from the detector controller 26 to the detector 14 approximately when the switch 13 is activated. Moreover, in the exemplary predetermined time period to delay the activation of the X-ray source 12 after the switch 13 has been activated is approximately equal to or greater than $T_S$ to enable the detector time to complete an on going scrubs of the detector 14. As discussed above, the time required to scrub the remaining portion of the detector 14 is no more than $T_S$. Therefore, after the switch 13 is activated, the detector 14 receives information from the detector controller 26 that the switch 13 has been activated. In response, the detector 14 has adequate time to complete an ongoing scrub prior to receiving the transmitted X-rays.

For example, referring to FIG. 7, the timing diagram 200 illustrates a first timing signal 210, a second timing signal 212, and a third timing signal 214. As discussed above, at 152, the detector 14 is initially configured to operate in an idle mode as shown by timing signal 214. In the idle mode of operation, the entire detector 14 is continually scrubbed to remove diode leakage and to maintain a known potential or a known voltage on the photodiodes 112 during idle periods as shown in timing signal 214. At 154, the detector controller 26 receives a signal from the switch 13 that the X-ray source 12 has been activated as shown by timing signal 210. At 156, the detector controller 26 transmits the signal to the detector 14 as shown by timing signal 214. At 158, the system controller (not shown) instructs the X-ray source 12 to begin transmitting X-rays to the detector 14 after the predetermined time-period $T_S$ as shown by timing signal 212.

Referring again to FIG. 6, at 160 the detector controller 26 determines if the x-ray exposure is completed and the information acquired by the detector 14 is read-out or transmitted to the detector controller 26 or the workstation 34 to generate an image of the object or patient. However, as discussed above, reading the detector 14 is performed whenever an image is acquired by the detector 14. However, because the detector 14 is not integrated with the X-ray source 12, the detector 14 described herein is unable to determine when the X-ray source 12 has completed radiating the patient or object and thus completed transmitting X-rays to the detector 14. Accordingly, the method described herein enables the detector controller 26 to periodically query or scan the detector 14 to determine if the exposure has been completed. As discussed above, reading or scanning the detector 14, prior to the exposure being completed, may result in information produced by the detector 14 being lost. As a result, useful diagnostic information may be discarded resulting in only a partial image or a degraded image. Therefore, determining at 160 whether the exposure of the object or subject is completed, and the X-ray source 12 has ceased transmitting X-rays, includes selecting at 162 an active imaging area and an inactive imaging area of the detector 14.

Figure 8:
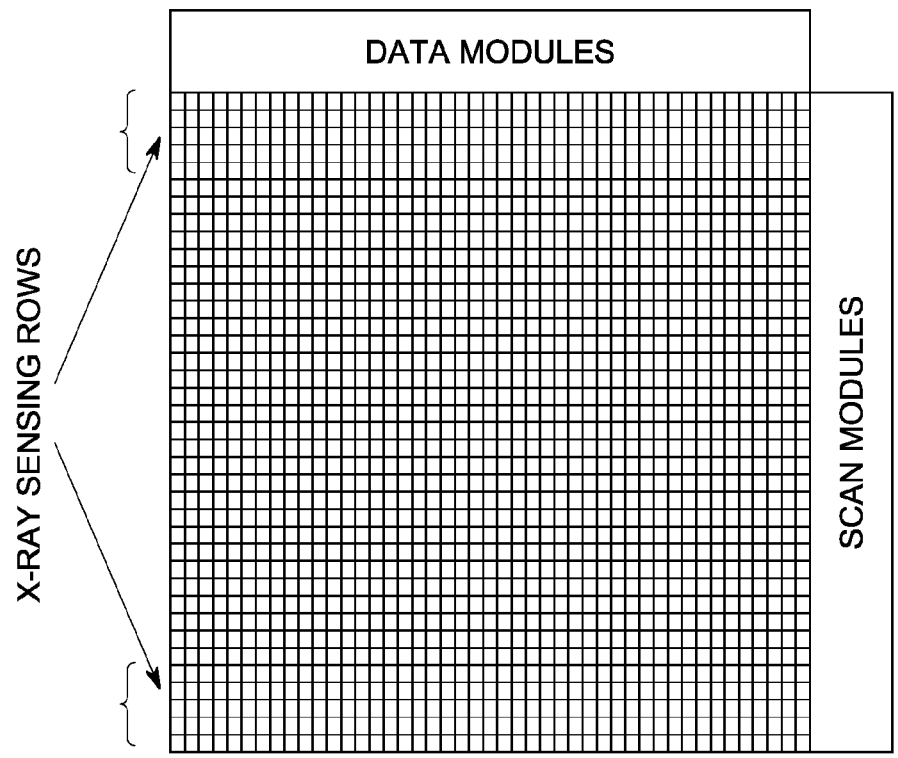
FIG. 8 illustrates an exemplary detector that includes an active area and a plurality of inactive areas in accordance with an embodiment of the present invention.

FIG. 8 illustrates an exemplary detector 14 that includes an active area 312 and an inactive area 314 and an inactive area 316. It should be realized that although the exemplary embodiment shown in FIG. 8 includes two inactive areas, a single inactive area or more than two inactive areas may be selected at 162. In general, the active area 112 represents the portion of the detector 14 that includes useful information for reconstructing an image of the subject. Whereas, the inactive areas 114 and 116 generate lower quality information that is used to determine whether the exposure of the object or subject is completed as is discussed in more detail below. In one embodiment, the active and inactive areas 112 and 114/116 may be selected based on previous operating knowledge of the detector 14. For example, based on previous operational knowledge it may be determined that counts recorded by pixels located nearest the edges of the detector 14 produce less useful information than rows located near the center of the detector 14. Thus, pixels located proximate to the edges of the detector 14 may be selected as inactive areas.

Figure 9:
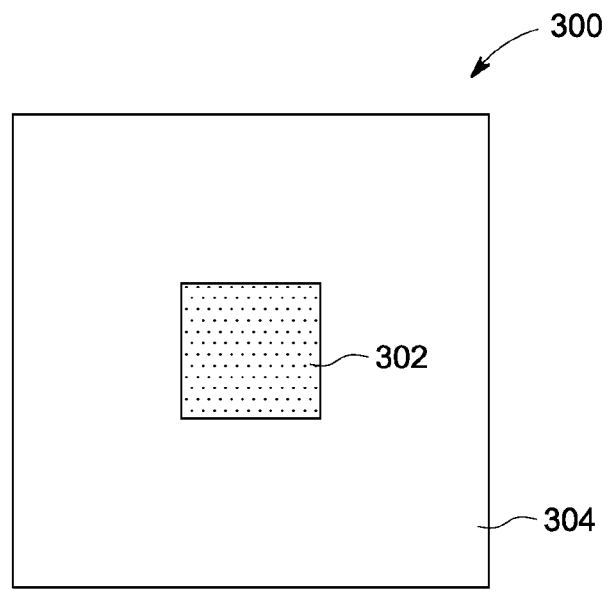
FIG. 9 is an exemplary image acquired by the detector shown in FIGS. 1-4 in accordance with an embodiment of the present invention.

For example, FIG. 9 is an image 300 acquired by the detector 14 using the collimator 20. A central portion 302 of the image, the gray scale image portion, represents the active area 312 having useful image data acquired during the scan of the subject. The outside portion 304 surrounding the central portion 302 represent information collected by the detector 14 that lies outside the collimated region, e.g. the central portion 302. In the case of FIG. 9, the central portion 302 would be the active portion 312 and the outside portion 304 would be the inactive areas selected at 162. As shown in FIG. 9, several inactive areas have been selected at 162.

Figure 10:
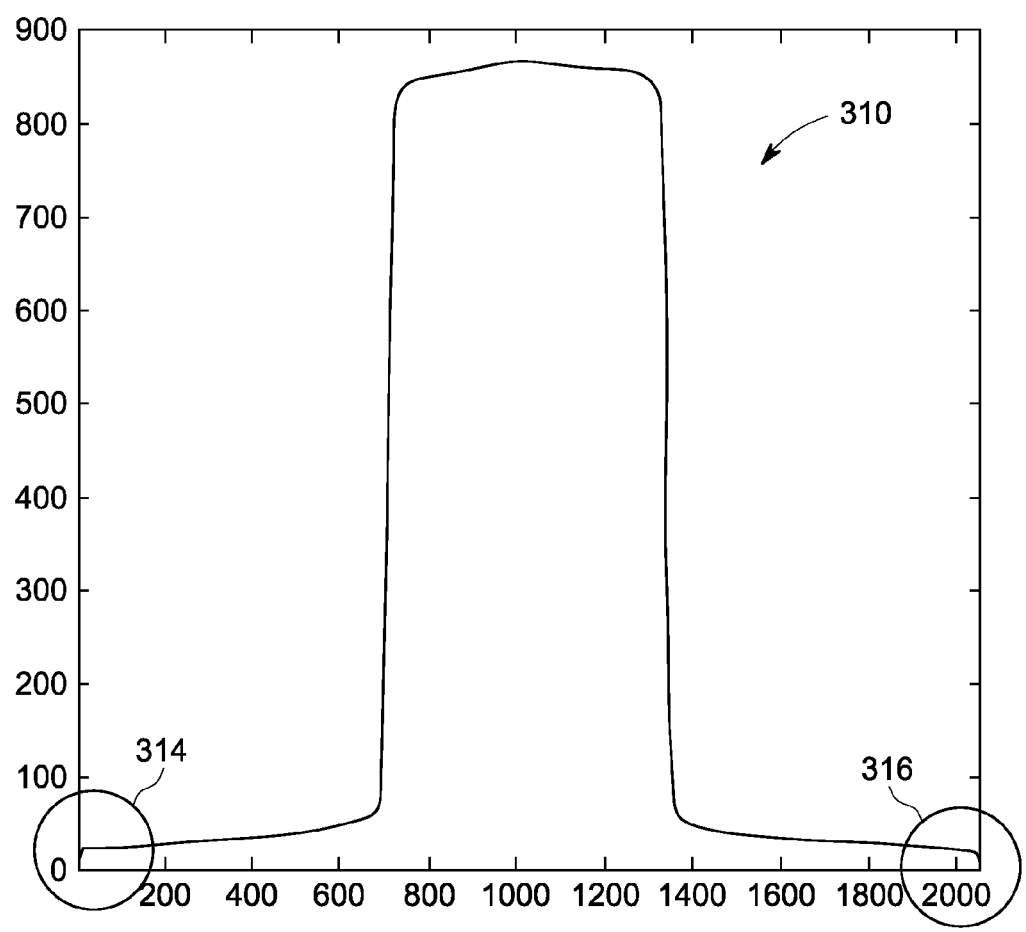
FIG. 10 is a graphical illustration of the information used to reconstruct the image shown in FIG. 9 in accordance with an embodiment of the present invention.

FIG. 10 is a graphical illustration showing a curve 310 of the pixel values, or counts, averaged by detector rows received from the detector 14 and used to reconstruct the image 300 shown in FIG. 9. The X-axis represents the detector row and the Y-axis represents detector counts. As shown in FIG. 10, the active area 312 includes counts greater than approximately 800 whereas two inactive areas 314 and 316 include less than one hundred counts. It should be realized that the total counts shown in FIG. 10 are averaged over the plurality of detector rows. Specifically, each of the detector rows in the inactive areas 314 and 316 recorded less than 100 counts. However, it should also be realized that although the information in the inactive areas 314 and 316 is not used to reconstruct an image of the subject, the information in inactive areas 314 and 316 is used to determine whether the radiation of the object or subject is completed, and the X-ray source 12 has ceased transmitting X-rays.

Figure 11:
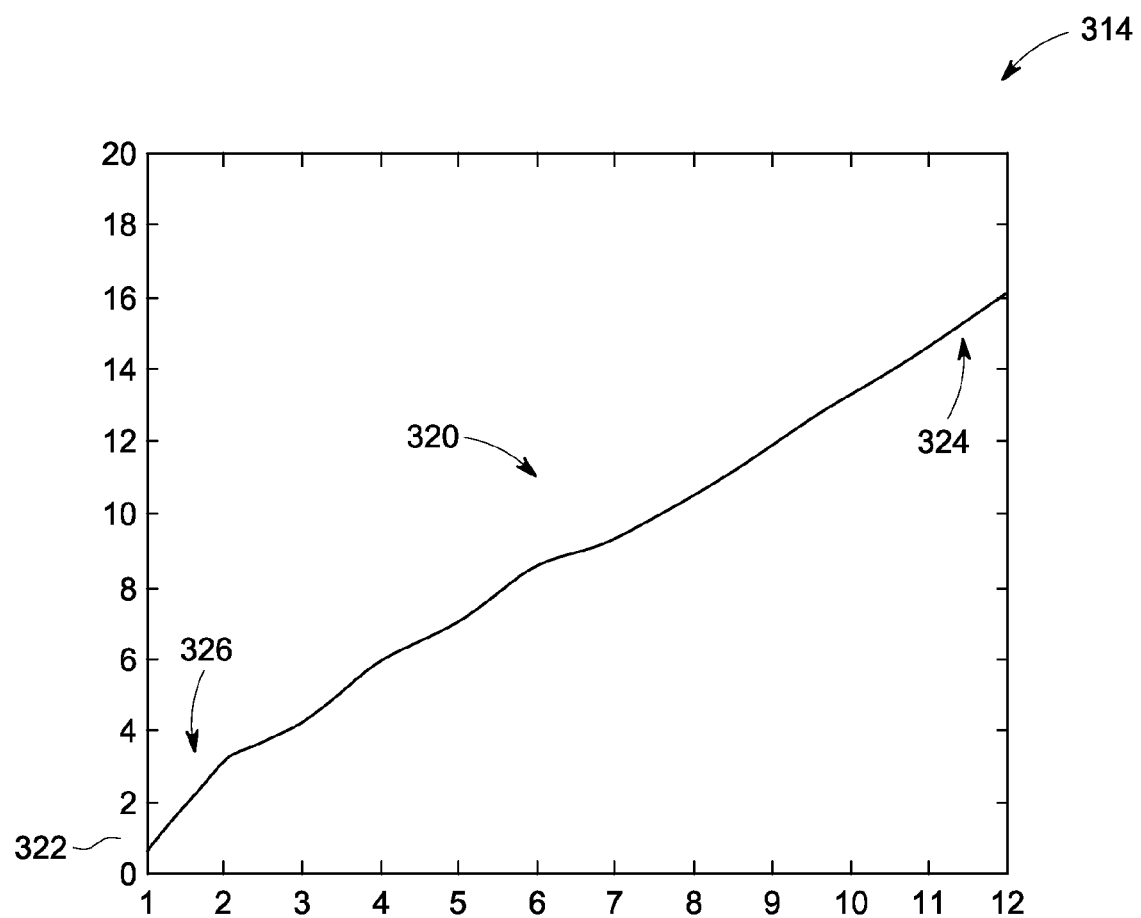
FIG. 11 is a graphical illustration of a portion of the information shown in FIG. 10.
Figure 12:
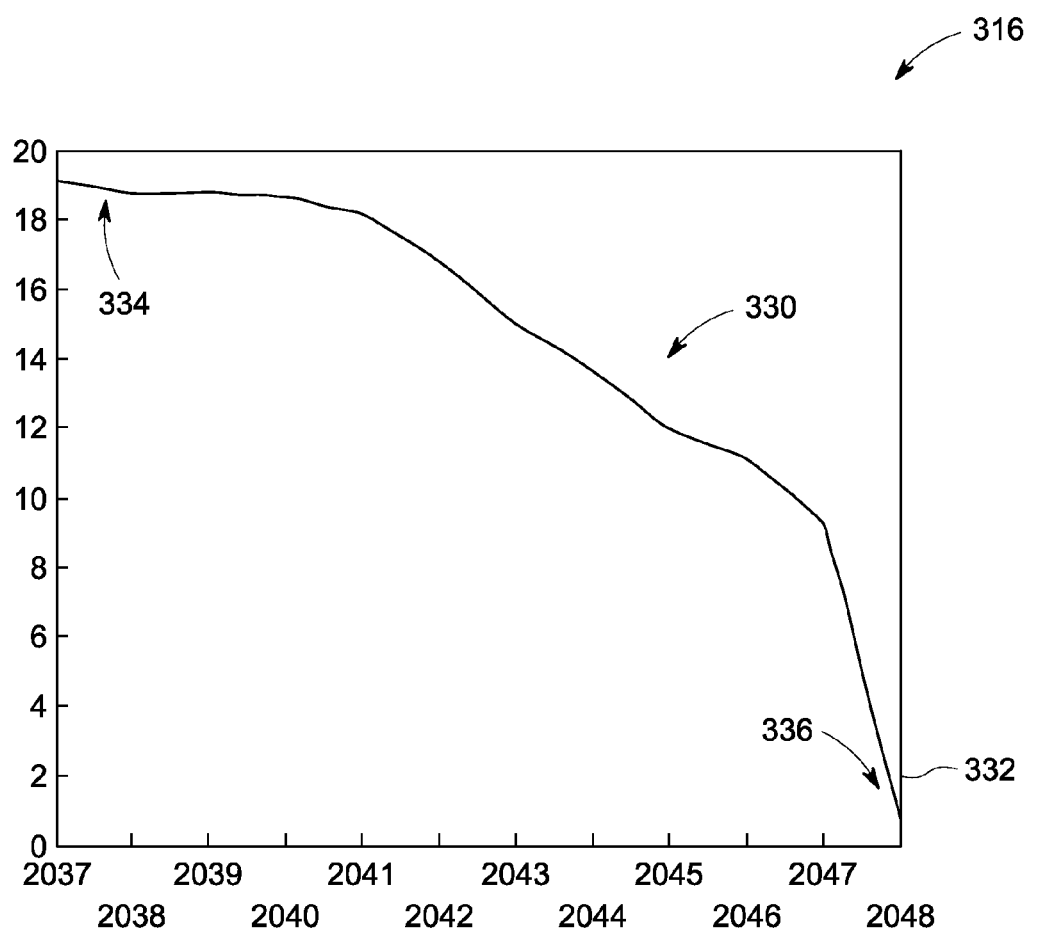
FIG. 12 is another graphical illustration of a portion of the information shown in FIG. 10.

For example, FIG. 11 is a graphical illustration of the counts recorded in the inactive area 314 and FIG. 12 is a graphical illustration of the counts recorded in the inactive area 316. As shown in FIG. 11, during operation, the total counts, as represented by the line 320 recorded by the detector 14 gradually decrease from an interior section of the detector, e.g. the active area 312, to a first edge 322 of the detector 14. For example, an interior row 324 has recorded approximately 16 counts, whereas an exterior row 326, at the edge of the detector 14, has recorded approximately 1 count. Moreover, as shown in FIG. 12, the total counts as represented by the line 330 recorded by the detector 14 gradually decrease from the interior section of the detector 14, e.g. the active area 312, to a second opposing edge 332 of the detector 14. For example, an interior row 334 has recorded approximately 19 counts, whereas an exterior row 336, at the edge of the detector 14, has recorded approximately 1 count. As shown in FIGS. 11 and 12, since the standard deviation of the electronic noise of the pixel value $\sigma_p$ is around 6000 electrons with ARC gain of approximately 4400 electrons/count, the standard deviation of the noise for the row-averaged pixel values $\sigma_r$ is $$\sigma_r = \frac{1}{\sqrt{2048}} \sigma_p = 0.02 \sigma_p = 120 e^- = 0.03 \text{ Count}$$

Therefore, the pixels in the inactive areas 314 and 316 are sensitive enough to detect the completion of the x-ray because approximately 20 counts with very low dose are recorded utilizing a relatively small collimator opening. Therefore, the selecting at 162 of the method 150 at FIG. 6, includes identifying an active imaging area that generates information used to reconstruct an image of the object being radiated Moreover, the selecting at 162 further includes identifying at least one inactive imaging area that generates information used to determine whether the radiation of the object has been completed.

Referring again to FIG. 6, at 164 the detector controller 26 determines if the X-ray radiation of the object has been completed. Specifically, the detector controller 26 reads the count information stored in at least one of the inactive areas 314 and/or 316. As discussed above, when the X-ray radiation operation is completed, the total counts recorded by the detector rows in the inactive areas gradually decreases to approximately zero. Accordingly, the detector controller 26 is programmed to determine when the counts in the inactive areas falls below a predetermined threshold thus indicating that the scan has been completed. In the exemplary embodiment, the predetermined threshold is less than approximately 100 counts. In this manner, the detector controller 26 may read the count information stored in at least one of the inactive areas 314 and/or 316 once, or may read the count information stored in at least one of the inactive areas 314 and/or 316 multiple times without destroying the information stored in the active area of the detector 14. Referring again to FIG. 7, in the exemplary embodiment, the detector controller 26 is configured to wait a predetermined time $T_D$ before reading the active areas of the detector to ensure the completion of the X-ray tail has been completed. In the exemplary embodiment, $T_D$ is selected to enable the detector 14 to have sufficient time to wait the tails of the X-rays 14.

Referring again to FIG. 6, in one embodiment, if the detector controller 26 has determined that the X-ray radiation is completed the method proceeds to step 166. At 166, the X-ray controller 26 reads out the information from the active area 312. The information from the active area 312 is then used to reconstruct an image of the object as shown in FIG. 7 on line 214. Optionally, referring again to FIG. 6, in another embodiment, if the detector controller 26 has determined that the X-ray radiation is not completed, the method proceeds to step 168.

At 168, the X-ray controller 26 determines whether a maximum exposure time has been exceeded. For example, as discussed above, at 158, the system controller instructs the X-ray source 12 to begin transmitting X-rays to the detector 14 after the predetermined time-period $T_S$. Additionally, the detector controller 26 activates a timing circuit (not shown) that indicates a time that the object is being exposed. At 168, when the exposure time has exceeded the predetermined threshold, the detector controller 26 reads the information stored in the active area 312 and reconstructs an image of the object.

Referring again to FIG. 7, after the method illustrated in FIG. 6 is completed, and the image information is read from the detector 14, the detector controller 26 scrubs the detector 14. Scrubbing is similar to reading except that data acquired from scrubbing is not used to reconstruct an image of the object, and is therefore discarded. Scrubbing is performed on the detector 14 to maintain proper bias on the photodiodes during idle periods, and/or to reduce a plurality of effects of lag, which is incomplete charge restoration of the photodiodes. Specifically, scrubbing is performed to keep the detector ready for use largely due to the less than ideal characteristics of amorphous silicon used to fabricate the detector. The detector 14 may be scrubbed once after the detector 14 is read. Optionally, the detector 14 may be scrubbed several times after the detector 14 is read.

After the completion of the scrubbing process, the detector controller 26 is configured to wait a period of time that is equal to the x-ray sensing time plus the x-ray tail time $T_D$ and then generate a dark image or an offset image. To generate a dark image, information from the detector 14 is read by the detector controller 14, but the X-ray source 12 is not activated. A pixel offset correction may then be performed using the dark image. For example, the pixel offset correction may be performed by subtracting the dark image, or optionally, an offset image, pixel values from the image pixel values obtained during the radiation scan.

Referring again to FIG. 7, after the offset correction is performed, the detector 14 is again placed in idle mode, and the detector controller 26 continues to scrub the detector 14 until the switch 13 is depressed. When the switch 13 is depressed, the method is repeated at step 155 as shown in FIG. 6.

Figure 13:
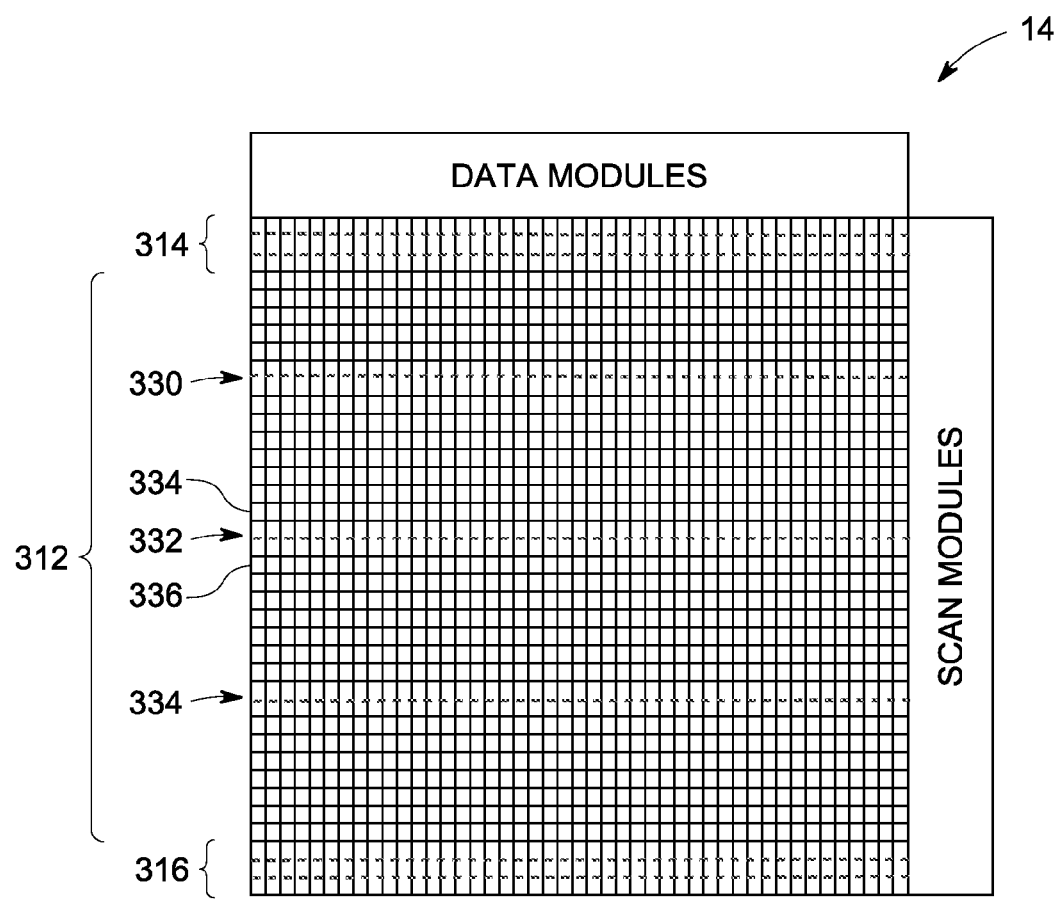
FIG. 13 illustrates another exemplary detector that includes an active area and a plurality of inactive areas in accordance with an embodiment of the present invention.

FIG. 13 illustrates another exemplary detector 14 shown in FIG. 8. As shown in FIG. 13, in this exemplary embodiment, the detector 14 includes the active area 312 and the inactive areas 314 and 316 each located proximate to the edge of the detector 14. Moreover, the detector 14 also includes at least one additional inactive area 330. Optionally, the detector 14 may also include additional inactive areas 332 and/or 334. In the exemplary embodiment, the detector 14 includes at least one inactive area 330, 332 and/or 334 that divides the active area 312 into a plurality of active areas. More specifically, as discussed above in FIG. 8, in one embodiment, the inactive areas 314 and 316 are located proximate to the edge of the detector 14 and the active area 312 is located near the center of the detector 14 where the most useful information from the imaged object is recorded. However, to facilitate determining when a radiation scan is completed at 164, the detector controller 26 may read the count information stored in at least one of the inactive areas 330, 332, and/or 334. As discussed above, when the X-ray exposure is completed, the detector controller 26 reads the count information retrieved from the active area 312. However, in this case, the active area 312 is divided into a plurality of active areas by one or more inactive area areas 330, 332, and/or 334. Therefore, to reconstruct an image of the object being radiated, the information that is lost when the inactive areas 314, 316, 330, 332, and/or 334 are read, are accounted for. In the exemplary embodiment, at least one row on each side of the inactive area is interpolated to form data that may be used to reconstruct an image of the object. For example, referring to FIG. 13, assume that the inactive area 332 is read to determine when the radiating procedure has concluded. In this case, the information from the inactive area 332 is not used to reconstruct an image of the object. Therefore, information from rows 334 and 336 may be interpolated to replace the information lost in the inactive area 332. The interpolated information is then combined with the information for the remainder of the active area 312 to generate an image of the object.

Described herein is a system and method for determining when an X-ray scan is completed using a portable detector 10. The X-ray detector is divided into active and inactive areas. The active areas are used to reconstruct an image of the object. The inactive areas are periodically scanned to determine when the X-ray source has completed transmitting X-rays to the detector, and thus completed the medical examination of the patient.

Some embodiments of the present invention provide a machine-readable medium or media having instructions recorded thereon for a processor or computer to operate an imaging apparatus to perform an embodiment of a method described herein. In the exemplary embodiment, the machine-readable medium is a tangible and non-transitory computer-readable medium. The medium or media may be any type of CD-ROM, DVD, floppy disk, hard disk, optical disk, flash RAM drive, or other type of computer-readable medium or a combination thereof.

A technical effect of the various embodiments is to enable an imaging system, that includes a portable X-ray detector that is not integrated with the X-ray source, to read the X-ray detector prior to the conclusion of the X-ray examination. Reading the X-ray detector prior to the conclusion of the X-ray examination enables the imaging system to determine when the X-ray radiation of the object or patient has been completed.

The various embodiments and/or components, for example, the monitor or display, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a floppy disk drive, optical disk drive, and the like. The storage device may also be other similar means for loading computer programs or other instructions into the computer or processor.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. For example, the ordering of steps recited in a method need not be performed in a particular order unless explicitly stated or implicitly required (e.g., one step requires the results or a product of a previous step to be available). While the dimensions and types of materials described herein are intended to define the parameters of the invention, they are by no means limiting and are exemplary embodiments. Many other embodiments will be apparent to those of skill in the art upon reviewing and understanding the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose various embodiments of the invention, including the best mode, and also to enable any person skilled in the art to practice the various embodiments, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A method for imaging an object, said method comprising:
    radiating the object of interest;
    selecting an active area and an inactive area on an imaging detector;
    determining when the radiation of the object is completed using information received from the inactive area of the imaging detector; and
    reconstructing an image of the object using information received from the active area of the imaging detector.

2. A method in accordance with claim 1 further comprising scanning the object of interest using a portable X-ray detector.

3. A method in accordance with claim 1 wherein selecting an inactive area further comprises selecting an inactive area that includes a plurality of rows of pixels located proximate to an edge of the imaging detector.

4. A method in accordance with claim 1 wherein selecting an inactive area further comprises selecting an inactive area that includes at least one row of pixels that divides the active area into a plurality of active areas.

5. A method in accordance with claim 1 further comprising:
selecting an inactive area that includes at least one row of pixels that divides the active area into a plurality of active areas;
interpolating the information corresponding to the selected inactive area to reconstruct an image of the object being scanned.

6. A method in accordance with claim 1 further comprising reconstructing an image of the object using information received only from the active area of the imaging detector.

7. A method in accordance with claim 1 further comprising determining when the radiation is completed using photon count information read from the inactive area of the imaging detector.

8. A method in accordance with claim 1 further comprising:
scrubbing the imaging detector;
determining when radiating the object of interest has been initiated using the imaging detector;
finishing scrubbing the imaging detector when radiating the object of interest has been determined; and
sensing a completion of the radiation after the scrubbing is finished.

9. A method in accordance with claim 1 further comprising reading an offset image from the X-ray detector.

10. A method in accordance with claim 1 further comprising:
determining when counts information received from the inactive area falls below a predetermined threshold; and
reading the counts information from the active area when the counts information obtained from the inactive area is below the predetermined threshold.

11. A medical imaging system comprising:
a portable X-ray detector configured to receive X-rays from an X-ray source; and
a detector controller coupled to the portable X-ray detector, the detector controller configured to:
determine when an X-ray exposure of an object has been initiated;
select an active area and an inactive area on an imaging detector;
determine when the X-ray exposure is completed using information received from the inactive area of the imaging detector; and
reconstruct an image of the object using information received from the active area of the imaging detector.

12. A medical imaging system in accordance with claim 11 wherein in the detector controller is further programmed to select an inactive area that includes a plurality of rows of pixels located proximate to an edge of the imaging detector.

13. A medical imaging system in accordance with claim 11 wherein in the detector controller is further programmed to select an inactive area that includes at least one row of pixels dividing the active area.

14. A medical imaging system in accordance with claim 11 wherein in the detector controller is further programmed to:
select an inactive area that includes at least one row of pixels that divides the active area into a plurality of active areas;
interpolate the information corresponding to the selected inactive area; and
reconstruct an image of the object being scanned using the information from the active area and the interpolated information.

15. A medical imaging system in accordance with claim 11 wherein in the detector controller is further programmed to:
determine counts information received from the inactive area falls below a pre-determined threshold; and
read the counts information from the active area when the counts information obtained from the inactive area is below the predetermined threshold.

16. A medical imaging system in accordance with claim 11 wherein in the detector controller is further programmed to:
scrub the portable X-ray detector
determine when the X-ray exposure has been initiated; and
finish the scrubbing the portable X-ray detector when X-ray exposure has been determined; and
monitoring the completion of the X-ray exposure.

17. A tangible and non-transitory computer-readable medium encoded with a program configured to:
determine when an X-ray exposure of an object has been initiated;
select an active area and an inactive area on an imaging detector;
determine when the exposure is completed using information received from the inactive area of the imaging detector; and
reconstruct an image of the object using information received from the active area of the imaging detector.

18. A non-transitory computer-readable medium in accordance with claim 17 wherein said program is further configured to:
select an inactive area that includes at least one row of pixels that divides the active area into a plurality of active areas;
interpolate the information corresponding to the selected inactive area; and
reconstruct an image of the object being scanned using the information from the active area and the interpolated information.

19. A non-transitory computer-readable medium in accordance with claim 17 wherein said program is further configured to:
determine when counts information received from the inactive area falls below a pre-determined threshold; and
read the counts information from the active area when the counts information obtained from the inactive area is below the predetermined threshold.

20. A non-transitory computer-readable medium in accordance with claim 17 wherein said program is further configured to:
determine when the scanning of the object of interest has been initiated; and
finish a scrubbing operation when scanning of the object of interest has been initiated.

* * * * *